United States Patent [19]
Linn et al.

[11] Patent Number: 5,833,964
[45] Date of Patent: Nov. 10, 1998

[54] ANTIPERSPIRANT STICK COMPOSITION

[75] Inventors: Elizabeth Linn, Lyndhurst; Consuelo P. de la Rosa, Nutley; Radhakrishna B. Kasat, Belle Mead; Morton L. Barr, East Brunswick, all of N.J.

[73] Assignee: Colgate-Palmolive Company, NY, N.Y.

[21] Appl. No.: 818,486

[22] Filed: Mar. 14, 1997

Related U.S. Application Data

[60] Provisional application No. 60/013,727, Mar. 20, 1996.

[51] Int. Cl.⁶ .................. A61K 7/32; A61K 7/34; A61K 7/36; A61K 7/38
[52] U.S. Cl. .................. 424/65; 424/66; 424/67; 424/68; 424/400; 424/401; 424/DIG. 5
[58] Field of Search .................. 424/65, 66, 67, 424/68, 400, 401, DIG. 5

[56] References Cited

U.S. PATENT DOCUMENTS

| | | | |
|---|---|---|---|
| 4,822,603 | 4/1989 | Farris et al. | 424/66 |
| 4,832,945 | 5/1989 | Osipow et al. | 424/65 |
| 4,840,789 | 6/1989 | Orr et al. | 424/66 |
| 4,853,214 | 8/1989 | Orr | 424/66 |
| 4,919,934 | 4/1990 | Deckner et al. | 424/401 |
| 4,985,238 | 1/1991 | Tanner et al. | 424/66 |
| 5,169,626 | 12/1992 | Tanner et al. | 424/66 |
| 5,225,188 | 7/1993 | Abrutyn et al. | 424/66 |
| 5,254,332 | 10/1993 | Grezcyn et al. | 424/66 |
| 5,302,381 | 4/1994 | Greczyn et al. | 424/66 |
| 5,449,511 | 9/1995 | Coe | 424/66 |
| 5,456,906 | 10/1995 | Powell et al. | 424/66 |
| 5,458,880 | 10/1995 | Kasat et al. | 424/401 |
| 5,531,986 | 7/1996 | Shevade et al. | 424/68 |

FOREIGN PATENT DOCUMENTS

| | | |
|---|---|---|
| 1 266 003 | 2/1990 | Canada . |
| 120210 A1 | 10/1984 | European Pat. Off. . |
| 388110 A1 | 9/1990 | European Pat. Off. . |
| 388111 A1 | 9/1990 | European Pat. Off. . |
| 396137 A1 | 11/1990 | European Pat. Off. . |
| 400546 A1 | 12/1990 | European Pat. Off. . |
| WO 94/22420 | 10/1994 | WIPO . |
| WO 95/27473 | 10/1995 | WIPO . |

OTHER PUBLICATIONS

Trade Literature: "Dow Corning 556 Cosmetic–Grade Silicone Fluid" 1983, Dow Corning Corporation, pp.:1–3.

Trade Literature: "Finsolv TN–Solubility in Water" 1993, *Finsolv TN*, pp.:1–3.

Trade Literature: "Kessco Peg 400 OS" 1996, *Stephan Product Bulletin*, pp.:1–2.

*Primary Examiner*—Shelley A. Dodson
*Attorney, Agent, or Firm*—Richard J. Ancel; Rosemary M. Miano; William I. Solomon

[57] ABSTRACT

Disclosed are antiperspirant stick compositions that exhibit substantially no visible residue (whitening) upon application to the skin or after drying. The compositions include both emollients that are silicone materials and emollients that are not silicone materials, these materials having a refractive index of at least 1.4460, in addition to including a vehicle (for example, cyclomethicone), a gelling agent (for example, stearyl alcohol and hydrogenated castor oil) and the active antiperspirant material (for example, particulate antiperspirant metal salts). These compositions reduce the necessity of using expensive silicone materials, while still achieving antiperspirant compositions with substantially no visible residue.

35 Claims, No Drawings

ANTIPERSPIRANT STICK COMPOSITION

BACKGROUND OF THE INVENTION

This application claims the benefit of U.S. Provisional application Ser. No. 60/013,727, filing date Mar. 20, 1996.

The present invention is directed to an antiperspirant stick composition. In particular, the present invention is directed to an antiperspirant stick composition (for example, a solid stick composition) which reduces or eliminates the residue left on the skin after application. Preferably the compositions of this invention leave substantially no visible (for example, white) residue on skin after application or after drying, and have superior cosmetic properties.

Wax-based stick compositions, which contain a wax-type solidifying agent, are known. It is also known to incorporate an antiperspirant active material, such as aluminum-zirconium-glycine complexes, in such wax-based stick compositions, to provide an antiperspirant stick. However, application of such wax-based antiperspirant stick to the skin frequently results in objectionable aesthetic characteristics (such as unsatisfactory glide on the skin); moreover, such products leave undesirable visible residue (white residue) on the skin after application and after drying.

U.S. Pat. No. 4,919,934 to Deckner, et al. discloses wax-based cosmetic stick compositions containing specific amounts of a wax-type solidifying agent and a polyalphaolefin, and preferably an active component such as a sunscreen agent, analgesic, antiperspirant or deodorant active. This patent discloses that the stick composition preferably also includes at least one emollient, selected from volatile and non-volatile silicone oils and non-polar fatty acid and fatty alcohol esters; these compositions which contain an antiperspirant active and/or deodorant active also preferably include at least one emulsifier. The contents of U.S. Pat. No. 4,919,934 are incorporated herein by reference in their entirety.

There have been attempts to provide low-residue antiperspirant solid sticks. See, for example, U.S. Pat. No. 4,822,603 to Farris, et al.; U.S. Pat. No. 5,254,332 to Greczyn, et al.; and U.S. Pat. No. 5,302,381 to Greczyn, et al. Each of U.S. Pat. No. 4,985,238 to Tanner and U.S. Pat. No. 5,169,626 to Tanner discloses low residue antiperspirant sticks containing specific amounts of a volatile silicone material; a particulate antiperspirant active; a low melting point wax; and a non-volatile paraffinic hydrocarbon fluid selected from mineral oils, branched-chain hydrocarbons containing an average of from about 16 to about 68 carbon atoms, and mixtures thereof. Non-essential components which can also be incorporated in the sticks include, for example, emollients, colorants, perfumes and emulsifiers.

U.S. Pat. No. 5,225,188 to Abrutyn, et al. discloses underarm formulations which contain volatile and/or non-volatile alkylmethylsiloxanes having a specific structure, which formulations may contain other components such as astringent antiperspirant compounds, suspending agents, conventional waxes, emollients, perfumes, coloring agents and other ingredients normally used in making underarm products. Incorporation of the alkylmethylsiloxanes in underarm formulations provide characteristics such as modified hardness, reduced whitening, improved feel, compatibility of ingredients, and control of vapor pressure.

It has also been proposed to incorporate phenyltrimethicone in antiperspirant formulations containing cyclomethicone as a vehicle, stearyl alcohol and hydrogenated castor oil as gelling agents, PEG-8 distearate, and aluminum-zirconium-tetrachlorohydrex-Gly, the phenyltrimethicone acting as a masking ingredient for the antiperspirant active ingredient to avoid a visible residue of the antiperspirant active on the skin.

U.S. Pat. No. 5,449,511 to Coe, the contents of which are incorporated herein by reference in their entirety, discloses a non-aqueous antiperspirant product that includes a non-aqueous carrier vehicle; an antiperspirant active salt suspended in particle form in the carrier vehicle; and a non-volatile, water-soluble, liquid (at 25EC) masking agent that interacts with the antiperspirant active to essentially eliminate discernible whitening without substantially inhibiting the antiperspirant activity of the salt when the product is applied to the skin. The masking agent can be selected from non-volatile aliphatic compounds (such as alcohols, ethers, silanols, silyl ethers, siloxanes and silicones) which contains disubstituted oxygen functionalities. This patent discloses that the masking agent preferably is a water-soluble, liquid, non-volatile emollient material, which reduces whitening by interacting with the particulates to produce an optical effect that tends to reduce light scattering and apparent whiteness. Illustrative masking agents disclosed in U.S. Pat. No. 5,449,511 include PPG-10 butanediol and dimethicone copolyols. This patent discloses that, in addition, for solid products, gelling agents may be included, examples of suitable gelling agents including hydrogenated castor oil, and fatty alcohols such as stearyl alcohol, among others, as well as blends and combinations.

Thus, it is an object of the invention to provide an antiperspirant stick composition that exhibits reduced and preferably no whitening (residue) upon application to the skin or after drying thereon, which has desired cosmetic properties and antiperspirant efficacy, and which can be formed at reduced cost.

It is also an object of the invention to provide antiperspirant stick compositions with reduced visible residue on the skin after application and after drying, which have good cosmetic characteristics.

It is a further object of the invention to provide an antiperspirant stick composition having reduced or substantially no visible (white) residue on the skin after application and after drying, which includes a method of making and of using such antiperspirant stick composition.

It is another object of the present invention to provide an antiperspirant stick composition which exhibits substantially little or no visible residue on the skin after application and after drying, and which has good cosmetic properties (including good glide on the skin and good emolliency).

SUMMARY OF THE INVENTION

The foregoing objects are achieved by an antiperspirant stick composition comprising:

(1) an antiperspirant active material;

(2) a gelling agent, in an amount so as to form a stick (especially a solid stick) product;

(3) a vehicle for the gelling agent, in an amount such that the gelling agent can dissolve therein and can gel therefrom; and (4) an emollient, including both at least one non-volatile silicone material and at least one non-volatile emollient material that is not a silicone material, wherein (a) both the at least one non-volatile silicone material and the at least one emollient material that is not a silicone material have a refractive index of at least 1.4460; and (b) these emollient materials, as a whole, are included in an amount so as to reduce or eliminate the whitening effect of an antiperspirant active ingredient on the skin.

DETAILED DESCRIPTION OF THE INVENTION

The present invention contemplates an antiperspirant stick composition that leaves substantially little or no visible residue (whitening) either upon application to the skin or after drying on the skin. The nonaqueous composition includes, in addition to an antiperspirant active material (for example, a particulate antiperspirant metal salt), a gelling agent, a vehicle for the gelling agent (the vehicle being a material in which the gelling agent can dissolve and from which the gelling agent can form a gel (for example, upon cooling)), and an emollient, the emollient including at least one non-volatile silicone material and at least one non-volatile emollient material that is not a silicone material, the various emollient materials having a refractive index of at least 1.4460, with the emollient materials being included in an amount so as to mask a whitening effect of the antiperspirant active ingredient (and any other whitening powder ingredient, such as talc) on the skin.

By incorporating the emollient material that is not a silicone material, such emollient material having the specified refractive index, especially in combination with the non-volatile silicone material, a relatively low-cost component can be included to mask any whitening effect, while also providing improved cosmetic properties due to its emolliency effects.

The antiperspirant active materials used in this invention can be any conventional antiperspirant material, including (but not limited to) antiperspirant active metal salts. These antiperspirant active metal salts generally have a refractive index of at least 1.500, and include, but are not limited to, aluminum-zirconium tri-, tetra- and penta-chlorohydrate glycine complexes, which are coordination complexes of aluminum-zirconium tri-, tetra- or penta-chlorohydrate and glycine in which some of the water molecules normally coordinated to the metal have been displaced by the glycine. Illustrative antiperspirant active metal salts include aluminum-zirconium tetrachlorohydrex gly (for example, Reach AZP-908 and Reach 908-0, each manufactured by Reheis Inc., Berkeley Heights, New Jersey, which are coordination complexes of aluminum-zirconium tetrachlorohydrate and glycine in which some of the water molecules normally coordinated to the metal have been displaced by the glycine. The present invention is not limited to use of aluminum-zirconium tetrachlorohydrex gly, and other antiperspirant active metal salts (such as aluminum chlorohydrate), and/or other antiperspirant active materials, can be utilized in the stick composition of the present invention.

Illustratively, antiperspirant solid stick compositions according to the present invention contain the antiperspirant active material in an amount of 10–30% by weight, of the total weight of the composition. Moreover, the preferred antiperspirant material particulate (for example, antiperspirant metal salt particulate) has a median particle size of less than 100 microns, a bulk density of 20–40 pounds/cubic foot and a spherical particle shape. Most preferred is a median particulate size of 5–40 microns, preferably 5–10 microns.

The gelling agent used in the composition of the present invention are those commonly known in the art. Examples include various waxes, including (but not limited to) hydrogenated castor oil, fatty alcohols such as stearyl alcohol, polyethylene, etc. For various gelling agents, attention is directed to the solidifying agents described in U.S. Pat. No. 4,919,934 to Deckner, et al., the contents of which have been incorporated herein by reference in their entirety. Various combinations, blends and mixtures of different materials can be utilized as the gelling agent according to the present invention. Illustratively, the gelling agent is included in an amount of 17%–40% by weight, of the total weight of the composition.

A preferred gelling agent for the present invention is a mixture of high melting point wax and low melting point wax, such as hydrogenated castor oil and stearyl alcohol, which respectively have refractive indices in the ranges of 1.570–1.585 and of 1.50–1.52. Any whitening effect due to the gelling agent can be avoided according to the present invention, utilizing emollient material having refractive indices of at least 1.4460.

Illustratively (and not limiting of the present invention), where the gelling agent includes both high and low melting point waxes, the low melting point wax is included in the composition in an amount of 10%–25% by weight, and the high melting point wax is included in the composition in an amount of 2%–17% by weight, each of the total weight of the composition.

Of course, the gelling agent must be soluble in the vehicle, and must be able to be gelled therefrom, for example, upon cooling of the composition after the composition has been heated in order to dissolve the gelling agent in the vehicle.

The gelling agents suitable for use with this invention include microcrystalline waxes, stearyl alcohol, hydrogenated castor oil, cetyl stearate, stearyl stearate, cetyl myristate, cetyl palmitate, and stearoxydimethionine.

Compositions according to the present invention include a non-aqueous carrier vehicle; in preferred embodiments, a volatile silicone such as cyclomethicone is utilized as the vehicle. An illustratively cyclomethicone which can be used as the vehicle is DC-345 silicone fluid, from Dow Corning Corp. However, the vehicle is not limited to cyclomethicone, and other known vehicles, such as aliphatic hydrocarbons, can also be utilized as the vehicle. Illustratively, and not limiting of the present invention, the vehicle is included in the composition in an amount of 30%–50% by weight, of the total weight of the composition.

Suitable vehicles include cyclomethicone, hydrogenated polyisobutene, isodecane, isohexane, and isoeicosane.

Emollients are a known class of materials in this art, imparting a soothing effect to the skin. According to the present invention, the emollient (for example, non-volatile emollient) incorporated in the composition both reduces or eliminates visible residue and imparts emollient effects to the skin. Suitable non-volatile emollients include silicone and non-silicone materials. Such silicone materials include silicone compounds such as phenyltrimethicone and dimethicone copolyol.

The non-volatile emollient materials (both the non-volatile silicone materials and the non-volatile emollient material that is not a silicone material) each can include a mixture. The emollient materials cannot all be silicone materials. It is preferred that each of the emollient materials of the mixture has a refractive index of at least 1.4460. Preferably, the emollient materials have a high refractive index, close to the refractive index of the antiperspirant active material.

By incorporating the emollient materials (including the emollient material that is not a silicone material) having a refractive index of at least 1.4460, in the composition, both improved cosmetic properties and reduced whitening effects are achieved. That is, by utilizing the emollient materials having the refractive index of at least 1.4460, whitening effects of the active salt complex (and any other whitening powder ingredient in the composition for example, talc) can be avoided. Moreover, the compositions, containing the at least one non-volatile emollient material that is not a silicone material, can include relatively inexpensive emollients.

Accordingly, through use of the present invention, incorporating at least the non-silicone, non-volatile emollient material having a refractive index of at least 1.4460 in the composition, in combination with the non-volatile silicone, an antiperspirant stick composition is achieved which exhibits no residue (whitening) upon application to the skin or after drying, which composition includes relatively low-cost materials, and which composition has good cosmetic properties.

The composition according to the present invention desirably includes, in addition to the foregoing components, inert fillers and/or other materials such as, for example, fragrances, bacteriostats and/or bactericides, colorants, etc., known in the art as components of antiperspirant stick compositions.

As mentioned previously, various known components of antiperspirant solid sticks can also be incorporated in the solid stick compositions according to the present invention, such known components including fragrances, bacteriostats, etc. Known bacteriostats include bacteriostatic quaternary ammonium compounds such as 2-amino-2-methyl-1-propanol (AMP), cetyl-trimethylammonium bromide, cetyl pyridinium chloride, 2, 4, 4N-trichloro-2N-hydroxydiphenylether (Triclosan), etc., and various zinc salts. The bacteriostat can, illustratively, be included in the composition in an amount of 0.2–1.0% by weight, of the total weight of the composition.

Various fragrances known in the art can also be incorporated in the antiperspirant solid stick composition of the present invention. These fragrances can be incorporated in amounts known in the art, e.g., 0.5–3.0% by weight, of the total weight of the composition.

Inert fillers can be incorporated in the antiperspirant stick compositions of the present invention. Illustratively, the inert filler can be corn starch, talc, fumed silica and/or inorganic clays, polyethylene, or mixtures of these inert particulate materials. Preferably, the inert filler, in particulate form, should have physical properties (for example, size, shape, etc.) that are similar to those of the antiperspirant active material (for example, particulate antiperspirant active metal salt).

Where the inert filler contributes to the whitening (visible residue) effect of the stick composition, the whitening effect can be reduced through use of the emollient having the refractive index in the present invention.

While the invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Throughout the present disclosure, where compositions are described as including or comprising specific components, or where processes are described as including or comprising specific processing steps, it is contemplated that compositions of the present invention also consist essentially of, or consist of, the recited components, and that the processes of the present invention also consist essentially of, or consist of, the recited processing steps.

In the following Table are set forth various illustrative non-volatile, non-silicone emollient materials that can be utilized, in combination with the non-volatile silicone emollient material, as part of the present invention, both to reduce the whitening effect of the antiperspirant active ingredient and to provide emollient properties to the antiperspirant stick compositions. Listed in the following Table are the CTFA name (as set forth in the *CTFA International Cosmetic Ingredient Dictionary* (4th Ed. 1991)), a trade name for the material (where appropriate), and the refractive index of such material.

TABLE

| CTFA Name | Tradename | Refractive Index |
|---|---|---|
| Isostearyl isostearate | SCHERCEMOL 1818 | 1.4612 |
| Glycereth-7-benzoate | PELEMOL G7B | 1.4953 |
| C12–C15 alkyl benzoate | FINSOLV TN | 1.4820 |
| Octyldodecyl benzoate | FINSOLV BOD | 1.4833 |
| Isostearyl lactate | PELEMOL ISL | 1.4519 |
| Isostearyl palmitate | DERMOL ISP | 1.4546 |
| Benzyl laurate | MAZON EE-1 | 1.4811 |
| Laureth 4 | MACOL LA 4 | 1.4514 |
| Laureth 7 | MACOL LA 790 | 1.4547 |
| Oleth 2 | BRIJ 93 | 1.4612 |
| PEG 4 | CARBOWAX 200 | 1.4594 |
| PEG 12 | CARBOWAX 600 | 1.4664 |
| PPG 2 ceteareth 9 | EUMULGIN L | 1.4611 |
| PPG 2 isodeceth 12 | SANDOXYLATE SX 424 | 1.4591 |
| PPG 5 buteth 7 | UCON 50 HB 170 | 1.4526 |
| PPG 14 butyl ether | FLUID AP | 1.4474 |
| PPG 15 butyl ether | UCON LB 285 | 1.4479 |
| PPG 53 butyl ether | UCON LB 3000 | 1.4512 |
| Octyldodecanol | EUTANOL G | 1.4530 |
| Polydecene | ETHYLFLO 364 | 1.4535 |
| Polydecene | ETHYLFLO 366 | 1.4569 |

Of course, combinations (for example, mixtures) of at least two of the above-listed emollient materials can be incorporated in compositions of the present invention.

Illustratively, the non-volatile emollient material that is not a silicone can be incorporated in the composition in an amount of 10%–27% by weight, of the total weight of the composition. This range is not limiting of the present invention.

Furthermore, compositions according to the present invention include non-volatile silicone emollient materials, for example, those having relatively high refractive indices (such as phenyltrimethicone, having a refractive index of 1.4600). Phenyltrimethicone is an illustrative non-volatile emollient silicone material, and is not limiting of the present invention. Illustratively (and not limiting), the non-volatile emollient silicone material is included in the composition in an amount of 5%–20% by weight, of the total weight of the composition. Combinations (such as mixtures) of at least two non-volatile emollient silicone materials can be incorporated in compositions of the present invention; thus, combinations both of non-volatile emollient materials and of non-volatile silicone emollient materials can be included in compositions of the present invention. Other emollient materials which can be incorporated in the compositions of the present invention include, illustratively (but not limiting), dimethicone copolyol (DC 190), having a refractive index of 1.4480; and dimethicone copolyol (DC 193), having a refractive index of 1.4540. Where relatively large amounts of the relatively expensive phenyltrimethicone, and where relatively large amounts of the dimethicone copolyols, are utilized, advantages of using the non-silicone material (for example, low-cost component) are somewhat limited.

The antiperspirant sticks of the present invention may be manufactured using methods known in the art. Typically, the ingredients are combined and heated to melt components (for example, other than the antiperspirant material particulate and particulate inert filler), and the melted and particulate components are mixed. Desirably, volatile materials, such as the fragrance material, are incorporated in the composition in the latter stages of the mixing cycle, in order to avoid volatilization thereof. After mixing, the molded composition can be poured into stick-form molds (for example dispensing containers), as conventional in the art, after which the compositions harden into a solid.

The compositions according to the present invention can be utilized by the consumer, to reduce perspiration, as conventional antiperspirant solid stick compositions are used. An end of the molded compositions, hardened in the dispensing container, can be elevated out of the dispensing container, so as to protrude out of the dispensing container, and rubbed against the skin in the axillary region, for example, so as to deposit antiperspirant active material in the axillary region, which prevents (or at least reduces) perspiration from the axillary region. Thus, by rubbing the composition of the present invention against the skin in regions of the body particularly prone to perspiration (for example, the axillary region), perspiration wetness in such regions can be controlled.

The following sets forth an example of the present invention. This example is illustrative, and not limiting, of the present invention. In this Example A, the amounts are in percent by weight, of the total weight of the composition. Where appropriate, the refractive indices of the various materials are set forth.

EXAMPLE A

| Ingredients | % w/w | Refractive Index |
| --- | --- | --- |
| Cyclomethicone | 37.0 | 1.3980 |
| PPG 14 Butyl Ether | 13.1 | 1.4474 |
| Phenyltrimethicone | 5.0 | 1.4600 |
| Aluminum Zirconium Tetrachlorohydrex Gly Complex | 20.0 | 1.5360 |
| PEG 8 Distearate | 2.0 | |
| Fragrance/Starch | 1.9 | |
| Hydrogenated Castor Oil | 4.0 | 1.570–1.585 |
| Stearyl alcohol | 17.0 | 1.50–1.52 |
| | 100.0% | |

In the foregoing Example A, PPG-14 butyl ether and phenyltrimethicone are used as emollient materials reducing the whitening effect of the whitening powder ingredients (for example, the antiperspirant active material) on the skin. It is preferred that emollients having relatively high refractive indices close to that of, for example, the antiperspirant active ingredient, be utilized, in order to avoid visible residue (whitening) on the skin.

EXAMPLE B

| Ingredients | % w/w | Refractive Index |
| --- | --- | --- |
| Cyclomethicone | 35.1 | 1.3980 |
| Phenyltrimethicone | 10.0 | 1.4600 |
| Aluminum Zirconium Tetrachlorohydrex Gly Complex | 20.0 | 1.5360 |
| PEG 8 Distearate | 2.0 | |
| Fragrance/Starch | 1.9 | |
| Hydrogenated Castor Oil | 4.0 | 1.570–1.585 |
| Stearyl alcohol | 17.0 | 1.50–1.52 |
| Isostearyl isostearate | 10.0 | 1.4612 |
| | 100.0% | |

Accordingly, by the present invention, an antiperspirant solid stick composition having substantially no visible (white) residue on the skin after application and after drying, and which has good cosmetic properties, yet which is relatively inexpensive in cost of the materials utilized to form the composition, is achieved.

Studies were done to illustrate the performance of compositions made in accordance with this invention. In the first study, a composition was made according to Example A and evaluated for visual white residue when applied to the underarm. Four commercial, white, opaque antiperspirant sticks and one antiperspirant gel product were also evaluated for comparison. There were five cells (each commercial product versus the Example A product; 14 female panelists participated in each cell. The evaluator applied 0.3 grams±10 percent of product in a circular motion into the armpit of the panelist. The panelist held her arms up for 30 minutes.

Then the evaluator standing 1.83 meters (6 feet)away from the panelist, ranked the intensity of whiteness seen in the 10 underarm area on a scale of 0–8 (0 being no whiteness and 8 being extreme whiteness). The evaluators were given photographs as standards for the scale. The results are listed below. In these tables, axillary vault area means a 10.16 cm×15.24 cm (4×6 inch) underarm area; n means the number of evaluations (for all the following tests n=14); p-value means the probability of observing a test statistic value which can be considered as extreme as, or more extreme than, the observed value The term "p-value" is recognized by those dealing with statistics Usually p-value is interpreted as a measure (on a scale from 0–1) of how well the data support or discredit the null hypothesis; the smaller the p-value, the greater the evidence against the null-hypothesis.

The "*" mark indicates a statistically significant difference favoring the product made by Example A.

| | Example A versus Commercial Sample B | | |
| --- | --- | --- | --- |
| Test Article | Mean | Difference (A vs. B) | p-value (A vs. B) |
| Example A | 0.43 | 0.86 | 0.001 |
| Sample B | 1.29 | | |

| | Example A versus Commercial Sample C | | |
| --- | --- | --- | --- |
| Test Article | Mean | Difference (A vs. C) | p-value (A vs. C) |
| Example A | 0.29 | 0.39 | 0.010 |
| Sample C | 0.68 | | |

-continued

Example A versus Commercial Sample D

| Test Article | Mean | Difference (A vs. D) | p-value (A vs. D) |
|---|---|---|---|
| Example A | 0.39 | 2.54 | <0.001 |
| Sample D | 2.93 | | |

Example A versus Commercial Sample E

| Test Article | Mean | Difference (A vs. E) | p-value (A vs. E) |
|---|---|---|---|
| Example A | 0.43 | 0.54 | 0.029 |
| Sample E | 0.96 | | |

Example A versus Commercial Sample F

| Test Article | Mean | Difference (A vs. F) | p-value (A vs. F) |
|---|---|---|---|
| Example A | 0.29 | 2.29 | <0.001 |
| Sample F | 2.57 | | |

In a second study, only the product of Example A was evaluated and similarly applied under both arms of 30 female panelists. This time the panelists held their arms at their sides for 30 minutes. Using the previously described 0–8 scale, the evaluator ranked the appearance of the underarm area. The average result was a value of 0.13, indicating very little visible white residue.

Although we have shown and described several embodiments in accordance with the present invention, it is understood that the same is not limited thereto, but is susceptible to numerous changes and modifications as known to one having ordinary skill in the art, and we therefore do not wish to be limited to the details shown and described herein, but intend to cover all such modifications as are encompassed by the scope of the appended claims.

What is claimed is:

1. Antiperspirant stick composition exhibiting reduced or no visible residue after application to human skin, comprising:
   (a) 10–30 weight % of an antiperspirant active ingredient;
   (b) a gelling agent, in an amount sufficient to provide the composition as a stick composition;
   (c) 30–50 weight % of a vehicle for the gelling agent selected from the group consisting of cyclomethicone, hydrogenated polyisobutene, isodecane, isohexane and isoeicosane; and
   (d) an emollient, the emollient comprising both at least one non-volatile silicone material and at least one non-volatile emollient material that is not a silicone material, wherein (i) the at least one non-volatile silicone material and the at least one non-volatile emollient material each have a refractive index of at least 1.4460, (ii) the non-volatile silicone material is added in an amount of 5–20 weight %, (iii) the non-volatile emollient that is not a silicone material is added in an amount of 10–27 weight %, and (iv) the emollient is included in an amount so as to reduce or eliminate a whitening effect of the antiperspirant active ingredient on the skin.

2. The antiperspirant stick composition according to claim 1, wherein the at least one non-volatile emollient material that is not a silicone is selected from the group consisting of isostearyl isostearate; glycereth-7-benzoate; $C_{12}$–$C_{15}$ alkyl benzoate; octyldodecyl benzoate; isostearyl lactate; isostearyl palmitate; benzyl laurate; laureth-4; laureth-7; oleth-2; PEG 4; PEG-12; PPG-2 Ceteareth-9; PPG-2 Isodeceth-12; PPG-5 buteth-7; PPG 14 butyl ether; PPG-15 butyl ether; PPG-53 butyl ether; octyldodecanol; and polydecene.

3. The antiperspirant stick composition according to claim 2, wherein the antiperspirant active ingredient is an antiperspirant metal salt, in particulate form.

4. The antiperspirant stick composition according to claim 3, wherein the antiperspirant active ingredient has a refractive index of at least 1.500.

5. The antiperspirant stick composition according to claim 4, wherein the antiperspirant active ingredient is aluminum-zirconium tetrachlorohydrex gly complex, having a refractive index of 1.5360.

6. The antiperspirant stick composition according to claim 4, wherein the non-volatile silicone material includes phenyltrimethicone.

7. The antiperspirant stick composition according to claim 6, wherein the composition also includes an additional whitening powder ingredient, the silicone material and the emollient material being included in an amount sufficient to reduce a whitening effect of the additional whitening powder ingredient and of the antiperspirant active ingredient on the skin.

8. The antiperspirant stick composition according to claim 6, wherein the gelling agent includes both stearyl alcohol and hydrogenated castor oil.

9. The antiperspirant stick composition according to claim 8, wherein the vehicle for the gelling agent includes cyclomethicone.

10. The antiperspirant stick composition according to claim 9, wherein the composition includes, in percent by weight of the total weight of the composition, 30%–50% of the vehicle, 2%–17% hydrogenated castor oil, 10%–25% stearyl alcohol, 10%–30% antiperspirant metal salt, 5%–20% non-volatile silicone material, and 10%–27% non-volatile emollient material.

11. The antiperspirant stick composition according to claim 1, wherein the antiperspirant active ingredient is an antiperspirant metal salt, in particulate form.

12. The antiperspirant stick composition according to claim 11, wherein the non-volatile silicone material includes phenyltrimethicone.

13. The antiperspirant stick composition according to claim 11, wherein the non-volatile silicone material includes dimethicone copolyol.

14. The antiperspirant stick composition according to claim 1, wherein the composition includes, in % by weight of the total weight of the composition, 5%–20% non-volatile silicone material and 10%–27% emollient material.

15. The antiperspirant stick composition according to claim 14, wherein the vehicle is included in an amount of 30%–50% by weight, the gelling agent is included in an amount of 17%–40% by weight, and the antiperspirant active ingredient is included in an amount of 10%–30% by weight, each of the total weight of the composition.

16. The antiperspirant stick composition according to claim 15, wherein the antiperspirant active ingredient is an antiperspirant metal salt, in particulate form.

17. A method for controlling perspiration wetness, comprising applying the antiperspirant stick composition of claim 16 to axillary regions of a human.

18. A method for controlling perspiration wetness, comprising applying the antiperspirant stick composition of claim 11 to axillary regions of a human.

19. A method for controlling perspiration wetness, comprising applying the antiperspirant stick composition of claim 10 to axillary regions of a human.

20. A method for controlling perspiration wetness, comprising applying the antiperspirant stick composition of claim 3 to axillary regions of a human.

21. A method for controlling perspiration wetness, comprising applying the antiperspirant stick composition of claim 1 to axillary regions of a human.

22. A method of reducing visible residue resulting from application of an antiperspirant stick composition to human skin, comprising incorporating an emollient in a composition also containing an antiperspirant active ingredient, a gelling agent and a vehicle for the gelling agent, wherein the emollient includes both at least one non-volatile silicone material and at least one non-volatile emollient material that is not a silicone material, the at least one non-volatile silicone material and the at least one non-volatile emollient material having refractive indices of at least 1.4460, wherein the emollient is incorporated in an amount so as to reduce a whitening effect of the antiperspirant active ingredient on the skin.

23. An antiperspirant stick composition made by combining:
(a) an antiperspirant active ingredient, in an amount sufficient to provide an antiperspirant active effect when applied to the human skin;
(b) a gelling agent, in an amount sufficient to provide the composition as a stick composition;
(c) a vehicle for the gelling agent, in an amount such that the gelling agent can dissolve therein and can gel therefrom; and
(d) an emollient, the emollient comprising both at least one non-volatile silicone material and at least one non-volatile emollient material that is not a silicone material, wherein (i) both the at least one non-volatile silicone material and the at least one non-volatile emollient material have refractive indices of at least 1.4460, and (ii) the emollient is included in an amount so as to reduce or eliminate a whitening effect of the antiperspirant active ingredient on the skin.

24. The antiperspirant stick composition according to claim 1 further comprising a bacteriostat.

25. The antiperspirant stick composition according to claim 24 wherein the bacteriostat is added in an amount of 0.2–1.0% by weight of the total weight of the composition.

26. The antiperspirant stick composition according to claim 24 wherein the bacteriostat is selected from the group consisting of quaternary ammonium compounds and zinc salts.

27. The antiperspirant stick composition according to claim 26 wherein the bacteriostat is selected from the group consisting of 2-amino-2-methyl-1-propanol; cetyl-trimethylammonium bromide; cetyl pyridinium chloride; and 2,4,4N-trichloro-2N-hydroxydiphenylether.

28. The antiperspirant stick composition according to claim 1 further comprising a fragrance.

29. The antiperspirant stick composition according to claim 28 wherein the fragrance is added in an amount of 0.5–3.0% by weight of the total weight of the composition.

30. The antiperspirant stick composition according to claim 1 further comprising an inert filler.

31. The antiperspirant stick composition according to claim 30 wherein the inert filler is selected from the group consisting of corn starch, talc, fumed silica, inorganic clays, polyethylene and mixtures of the foregoing.

32. The antiperspirant stick composition according to claim 30 comprising cyclomethicone, PPG-14 butyl ether; phenyltrimethicone; aluminum zirconium tetrachlorohydrex glycine complex; PEG-8 distearate; fragrance; starch; hydrogenated castor oil; and stearyl alcohol.

33. The antiperspirant stick composition according to claim 30 comprising cyclomethicone; phenyltrimethicone, aluminum zirconium tetrachlorohydrex glycine complex; PEG-8 distearate; fragrance; starch; hydrogenated castor oil; steaiyl alcohol; and isostearyl isostearate.

34. The antiperspirant stick composition according to claim 2 wherein the at least one non-volatile emollient material is $C_{12}$–$C_{15}$ alkyl benzoate.

35. The antiperspirant stick composition according to claim 34 further comprising a bacteriostat.

* * * * *